US009872831B2

(12) United States Patent
De Santis (10) Patent No.: US 9,872,831 B2
(45) Date of Patent: Jan. 23, 2018

(54) PHARMACEUTICAL COMPOSITION OF OXIDISED AVIDIN SUITABLE FOR INHALATION

(75) Inventor: Rita De Santis, Pomezia (IT)

(73) Assignee: ALFASIGMA S.P.A., Milan (MI) (IT)

( * ) Notice: Subject to any disclaimer, the term of this patent is extended or adjusted under 35 U.S.C. 154(b) by 0 days.

(21) Appl. No.: 14/236,445

(22) PCT Filed: Jul. 25, 2012

(86) PCT No.: PCT/EP2012/064576

§ 371 (c)(1),
(2), (4) Date: Jan. 31, 2014

(87) PCT Pub. No.: WO2013/017494

PCT Pub. Date: Feb. 7, 2013

(65) Prior Publication Data

US 2014/0134106 A1 May 15, 2014

(30) Foreign Application Priority Data

Aug. 2, 2011 (EP) .................................... 11006338

(51) Int. Cl.

| | |
|---|---|
| *A61K 9/00* | (2006.01) |
| *B82Y 5/00* | (2011.01) |
| *A61K 38/17* | (2006.01) |
| *A61K 51/04* | (2006.01) |
| *A61K 47/42* | (2017.01) |
| *A61K 47/66* | (2017.01) |

(52) U.S. Cl.

CPC ........ *A61K 9/0078* (2013.01); *A61K 38/1703* (2013.01); *A61K 47/42* (2013.01); *A61K 47/665* (2017.08); *A61K 51/0453* (2013.01); *B82Y 5/00* (2013.01)

(58) Field of Classification Search

None

See application file for complete search history.

(56) References Cited

U.S. PATENT DOCUMENTS

| | | | | |
|---|---|---|---|---|
| 5,384,128 | A * | 1/1995 | Meezan et al. | 424/450 |
| 2002/0137125 | A1* | 9/2002 | Zhu | 435/68.1 |
| 2006/0251579 | A1* | 11/2006 | Paganelli | A61K 31/4188 424/1.49 |
| 2010/0239497 | A1* | 9/2010 | DeSantis et al. | 424/1.69 |

FOREIGN PATENT DOCUMENTS

| | | |
|---|---|---|
| EP | 2106806 | 10/2009 |
| WO | 2009016031 | 2/2009 |

OTHER PUBLICATIONS

Tseng et al. Targeting efficiency and biodistribution of biotinylated-EGF-conjugated gelatin nanoparticles administered via aerosol delivery in nude mice with lung cancer. 2008 Biomaterials 29: 3014-3022.*

Modjtahedi et al. Phase I trial and tumour localisation of the anti-EGFR monoclonal antibody ICR62 in head and neck or lung cancer. 1996 Br. J. Cancer 73: 228-235.*

Haranaka et al. Antitumor activity of murine tumor necrosis factor (TNF) against transplanted murine tumors and heterotransplanted human tumors in nude mice. 1984 Int. J. Cancer 34: 263-267.*

Arenberg et al. The murine CC chemokine, 6C-kine, inhibits tumor growth and angiogenesis in a human lung cancer SCID mouse model. 2001 Cancer Immunol. Immunother. 49: 587-592.*

Boerman Otto C., et al., Pretargeted Radioimmunotherapy of Cancer . . . , The Journal of Nuclear Medicine, vol. 44, No. 3, 2003.

International Search Report issued in counterpart PCT Application No. PCT/EP2012/064576, dated Oct. 9, 2012.

Written Opinion of International Searching Authority issued in counterpart PCT Application No. PCT/EP2012/0645767, dated Oct. 9, 2012.

* cited by examiner

*Primary Examiner* — Michael G Hartley
*Assistant Examiner* — Jennifer Lamberski
(74) *Attorney, Agent, or Firm* — Lucas & Mercanti, LLP

(57) ABSTRACT

The present invention describes oxidized avidin, suitable for inhalation, for conditioning the lung affected by inoperable/diffuse diseases, enabling the targeted delivery of biotinylated therapeutic agents to it.

6 Claims, 10 Drawing Sheets

PHARMACEUTICAL COMPOSITION OF OXIDISED AVIDIN SUITABLE FOR INHALATION

This application is a U.S. national stage of PCT/EP2012/064576 filed on Jul. 25, 2012, which claims priority to and the benefit of European Application No. 11006338.5, filed on Aug. 2, 2011, the contents of each of which are incorporated herein by reference.

FIELD OF INVENTION

The invention described herein relates to a new pharmaceutical formulation of an oxidized avidin or biotinylated therapeutic agent/oxidized avidin complex for use by inhalation. It further relates to biotinylated therapeutics for targeting preconditioned lungs of mammals affected by inoperable and/or diffuse diseases.

BACKGROUND OF THE INVENTION

Inhalation of nebulised therapeutics has become a frequent drug delivery method for the treatment of lung diseases such as asthma or lung infections and other respiratory diseases. However, such mode of administration usually requires repeating the treatment several times per day, which however, may not be always compliant with patient's health conditions depending on the disease he suffers from or the grade of severity of the disease itself. Frequent inhalations of therapeutic agents also constitutes a severe life-limiting stress. Continuous nebulisation therapy of β2 agonists has proved to be a useful alternative therapy for patients suffering from severe asthma (Raabe O. G., et al., *Ann. Allergy Asthma Immunol.*, 1998, 80, 499). However, even in this case, the therapy is very time consuming and renders the patient's life uncomfortable.

Serious lung diseases such as lung cancer or cystic fibrosis are anyway still largely treated by systemic therapies which are unfortunately associated to significant side effects.

Lung's anatomy and physiology are well adapted to process exogenous nebulised substances for clearance in order to protect the organ. It is also recognized that also in the case of volunteer treatment exposure through inhalation of therapeutic agents, the latter are fast cleared therefore influencing negatively and thereby limiting the benefit of inhalation therapy.

It is further well known that enzymes aimed at detoxifying organs from external aggression are also present in the lung. Some of those which play an important role in the lung belong to the super family of proteins (i.e., AKR). AKR and short-chain dehydrogenases/reductases (i.e., SDRs) are the main enzymes that catalyze oxidation-reduction reactions involving a xenobiotic carbonyl. Among SDR superfamily, carbonyl reductases (i.e., CBRs) exhibit broad substrate specificity for carbonyl bearing xenobiotics (Matsunaga T., et al., *Drug Metab. Pharmacokinet.*, 2006, 21, 1, 1).

Attempts of local delivery of chemotherapeutics by aerosol have been recently reported in pre-clinical models of lung cancer showing reduced toxicity compared to systemic administration (Fulzele, S. V., et al., *J. Pharm. Pharmacol.*, 2006, 58, 3, 327).

A dry powder formulation for inhalation of temozolomide has recently been reported. The latter required a particle size reduction to enable a 51% release of the administered dose (Wauthoz N., et al., *Pharm. Res.*, 2011, 28, 762), and also the presence of biocompatible and biodegradable phospholipids as surfactants to stabilise the aqueous temozolomide suspension (Wauthoz N., et al., *Eur. J. Pharm. Sci.*, 2010, 39, 402).

A Phase I clinical trial involving cisplatin was conducted positively in order to investigate the safety and pharmacokinetics of aerosolized Sustained Release Lipid Inhalation Targeting (SLIT) cisplatin in patients with lung carcinoma. However, still quite a lot of side effects (i.e., nausea, vomiting, dyspnea, fatigue and hoarseness) were encountered in this study (Wittgen B. P. H., et al., *Clin. Cancer Res.*, 2007, 13, 2414).

Nebulisation of 5-fluorouracil in dogs demonstrated that the drug could reach very high concentrations mainly in the trachea, to a less extent but still important into bronchi and oesophagus and a reduced concentration (i.e., one fiftieth of the one encountered in the trachea) into the lymph nodes at the bronchial level (Tatsumura T., et al., *Br. J. Cancer*, 1993, 68, 1146).

Nevertheless, diffusion of these aerosolized small chemical drugs to the blood is still a relevant issue together with the need of repeated administration due to the short lung half life of these molecules.

Aerosol gene delivery is another application long pursued for the targeted therapy of lung diseases. After the cloning of the cystic fibrosis gene, there was great interest in the non-invasive delivery of genes directly to the pulmonary surfaces by aerosol. This approach could have application to inoperable pulmonary cancers as well and most early efforts focused mainly on the use of nonviral vectors, primarily cationic lipids and other formulation excipients (Densmore C. L., et al., *J. Gene Med.*, 1999, 1, 4, 251; Densmore C. L., et al., *Mol. Ther.*, 2000, 1, 2, 180).

Unfortunately, nebulisation shear forces, and inefficient pulmonary uptake and residence of aerosolized protein therapeutics coupled to low expression of genetic vectors have generally resulted in a poor therapeutic effect (Schwarz, L. A., et al., *Hum. Gene Ther.*, 1996, 7, 731). Consequently, the interest in lung delivery of protein-containing biologically active derivatives by aerosol has diminished in recent years.

If inhalation of therapeutic proteins had been sought as an attractive solution for targeted therapy of the lung, the formulation of protein to be nebulised still remains challenging. Indeed, in order for the aerosolized substance to penetrate the lungs in-depth, formulation requiring scrupulous selection of additives and particle size (i.e., up to 3 μm) have to be adjusted meticulously (Choi W. S., et al., *Proc. Natl. Acad. Sci.*, 98, 20, 11103). Furthermore, the quaternary, but also the secondary and tertiary structure of the protein can be altered by the nebulisation process. To overcome this drawback, Arakawa T., et al. disclosed the use of polyethylene glycol and/or a surfactant to preserve said structural conformation prior to nebulisation (WO199503034).

Variously grafted nanoparticles designed for aerosol administration to target the lungs and which can entrapped different anti-cancer drugs have also been described lately, but were reported to present some inflammatory disadvantages (Dailey L. A., et al., *Toxicol. Appl. Pharmacol.*, 2006, 215, 1, 100).

A polymer-based nanoparticle delivery system for inhalation has been disclosed recently (WO2009121631), wherein particles were administered by endotracheal instillation to mice.

Borlak J., et al. (EP2106806), described an improved drug delivery system to the lung consisting of:
 a polymer-based nanoparticle,
 a maleimide-based molecular linker, a targeting agent such as an antibody, a low molecular weight compound or a protein (preferably covalently linked to the linker), a drug.

Such nanoparticles had a mean size of 150 to 180 nm. According to the inventors, such delivery system took advantage of the molecular linker having a lipophilic portion which non-covalently anchors to the particle's polymeric matrix and a second portion comprising a maleimide compound to which it is possible to bind a targeting agent. Still according to the inventors, the targeting agent could be a member of a binding couple such as avidin-biotin. However, the specific embodiment involving avidin-biotin was not described in an enabling manner in this document.

Ethanol based formulations have been previously reported to be suitable for nebulisation of proteins with biological activity including enzymes (Choi W. S., et al., *Proc. Natl. Acad. Sci.*, 2001, 98, 20, 11103). However, very limited exposure to inhaled ethanol is disclosed (i.e. 10 minutes) since longer inhalation period can provoke inflammatory side effects.

Therefore and as alluded herein-above, the physical stresses inherent to nebulisation, coupled to the formation of a large area of air-water interface, can destabilize the structure of many proteins.

[$^{111}$In]-avidin and [$^{99m}$Tc]-biotin-liposomes administration through the pleural route has been disclosed and proved to be a better route to target lung mediastinal nodes than intraperitoneal route (Medina L. A., et al., *Nucl. Med. Biol.*, 2004, 31, 1, 41). However, injection in the pleural cavity implies an invasive procedure and is not adequate to obtain homogenous distribution in the lung tissue. In fact, the intention of Medina's work was to target mediastinal lymph nodes. Moreover, the radiolabelled biotin needed to be formulated in liposome to improve pharmacokinetic and pharmacodynamic features.

Therefore, there is a strong medical need in providing specific way of administration to directly deliver to the diseased lung an efficacious amount of therapeutic agent in order to avoid the bottlenecks associated with:

oral delivery (e.g., drug permeability issues, first-pass effect); and/or other systemic drug delivery routes which can be correlated to severe if not compromising toxic side effects and/or high clearance issues; and/or instability of the therapeutic according to its administration route and/or metabolic process; and/or multiple administrations of the therapeutic every day It has now been surprisingly found that The oxidized avidin, administered by inhalation, link to the surface of lung epithelial cells uniformly down to the alveoli, and that it does not surprisingly bind to the respiratory upper track (e.g., trachea).

This finding was completely unexpected since The oxidized avidin did not bind to tissue surfaces like skin, eye or bladder unless a damage was procured to said surfaces. It was also surprising that such mode of administration preserves the chemical integrity of the protein.

DESCRIPTION OF THE INVENTION

The present invention regards a pharmaceutical inhalable composition comprising an oxidized avidin or a biotinylated therapeutic agent/oxidized avidin complex, for targeted delivery of biotinylated therapeutics by inhalation to the lung. It further deals with the aerosol delivery of an oxidized avidin as a tool for conditioning the lung to accept a stable linkage of biotinylated therapeutics useful for the treatment of lung cancer, asthma, tuberculosis, Chronic Obstructive Pulmonary Disease (COPD), lung alveolitis, cystic fibrosis and alpha-1-antitrypsin deficiency.

Biotinylation of proteins, cells and nucleic acid is a biochemical procedure well known in the art. It can be performed by a number of different commercially available reagents reacting with different groups (i.e. primary and second amines, sulphydryl and carboxyl groups, etc). Biotinylation reagents are designed to be very flexible (long spacers to reduce steric hindrance) or to be releasable (to free active moieties) and have been extensively used for targeting functional biotinylated moieties to proteins of the avidin family. In particular, protein biotinylation has been extensively applied to monoclonal antibodies and other functional proteins (Bayer E. A., et al., Methods Enzymol, 1990b, 184, 138).

Suitable biotinylated anti-cancer therapeutics are for example chosen from the group comprising IgG1 monoclonal antibody that binds specifically to the epidermal growth factor receptor (EGFR) such as biotinylated cetuximab (Hama Y., et al., *Cancer Res.*, 2007, 67, 3809). Further biotinylated anti-cancer therapeutics are for example biotinylated adducts of anti c-Met antibody (Stella G. M., et al., *Expert. Opin. Investig. Drugs*, 2010, 19, 11, 1381); anti-HGF (Okamoto W., et al., *Mol. Cancer Ther.*, 2010, 9, 10, 2785); anti-CTLA4 (Di Giacomo A. M., *Cancer Immunol. Immunother.*, 2009, 58, 8, 1297); anti-VEGF (Ferrara N., et al., *Biochem. Biophys. Res. Commun.*, 2005, 333, 2, 328); anti-EpCAM (Kurtz J. E., et al, *Expert. Opin. Biol. Ther.*, 2010, 10, 6, 951); anti-HER2 monoclonal antibodies (Smith B. L., et al., *Br. J. Cancer*, 2004, 91, 6, 1190); TNF (Balkwill F., *Nat. Rev. Cancer*, 2009, 9, 5, 361), TRAIL (Kim T. H., et al., *Bioconjug. Chem.*, 2011,); or other cytokines like IL-2 (Herberman R., *Cancer Invest.*, 1989, 7, 5, 515; Koten J. W., et al., *Cytokine*, 2003, 24, 3, 57); G-CSF (Cavalloni G., et al., *Anticancer Drugs*, 2008, 19, 7, 689); GM-CSF (He Q., et al., *Cancer Immunol. Immunother.*, 2011, 60, 5, 715); IL-12 (Penichet M. L., et al., *J. Immunol. Methods*, 2001, 248, 1-2, 91; Adris S., et al., *Cancer Res.*, 2000, 60, 23, 6696); gamma interferon (Weiner L. M., Mol. Biother., 1991, 3, 4, 186). Such therapeutics are known to block tumour cell replication, induce tumour cell death and/or stimulate an anti-cancer immune response. Nevertheless, toxic side effects are associated to their systemic use. Therefore, stable localization within the lung of the biotinylated therapeutic agent upon:

its aerosol delivery following oxidized avidin inhalation, or upon inhalation of a biotinylated therapeutic agent/oxidized avidin complex whenever nebulisation is compatible with the integrity and biological function of either the therapeutic agent itself or of the complex; or upon its systemic delivery (e.g., parenteral administration) following oxidized avidin inhalation, will allow to reduce their therapeutic dose and minimize systemic exposure thus improving their therapeutic index. The present invention also deals with nebulised oxidized avidin for use in lung targeting of biotinylated anti-cancer effector cells, viral or plasmid vectors (D'Atri S., et al., *Immunopharmacol.*, 1991, 21, 3, 199; Densmore C. L., *Curr. Cancer Drug Targets*, 2003, 3, 4, 275).

The present invention further deals with the aerosol delivery of oxidized avidin as a useful tool for conditioning the lung to accept a stable linkage of anti-inflammatory biotinylated therapeutics. Suitable anti-inflammatory biotinylated therapeutics includes for example biotinylated adducts of anti-TNF, anti-Tweak, anti-IL-6, anti-IL-23, anti IL-17 monoclonal antibodies; IL-10 or other anti-inflammatory cytokines (Marchi E., et al., *Chest,* 2011) or chemokines (Farberman M. M., et al., *Am. J. Respir. Cell Mol. Biol.,* 2010; Tauler J., et al., *Curr. Opin. Pharmacol.,* 2009, 9, 4, 384; Hartl D., et al., *Curr. Opin. Allergy Clin. Immunol.,* 2009, 9, 1, 60; Brennan S., et al., *Eur. Respir. J.,* 2009, 34, 3, 655) for the treatment of asthma or lung alveolitis or other forms of lung chronic inflammation. Delivery of biotinylated enzymes like alpha-1-antitrypsin to the lungs via oxidized avidin nebulisation is also envisaged to cure primary genetic deficiency (Brand P., et al., *Eur. Respir. J.,* 2009, 34, 2, 354; Geller D. E., et al., *J. Aerosol Med. Pulm. Drug Deliv.,* 2010, 23 Suppl 1, S55) and Cystic Fibrosis Transmembrane Conductance Regulator (CFTCR) protein to cure cystic fibrosis (Sloane P. A., et al., *Curr. Opin. Pulm. Med.,* 2010, 16, 6, 591; Frizzell R. A., *Am. J. Respir. Crit. Care Med.,* 1995, 151, S54).

The avidin-biotin system has been known for many years as an exceptional tool for qualitative and quantitative studies in interactions between small molecules and biological receptors (Wilchek, M., *Methods Enzymol.,* 1990, 184, 14).

Avidin is a glycoprotein of about 68 kDa present in the poultry egg white and showing high affinity for the vitamin H biotin. Its dissociation constant ($K_d$~$10^{-15}$M) is the lowest known in nature (Green, N. M., *Adv. Protein Chem.,* 1975, 29, 85; Hytonen V. P., et al., *Biochem. J.,* 2003, 372, Pt1, 219). It is composed of four subunits of identical amino acid sequence, each of which can potentially bind one molecule of biotin. Glycosylation accounts for about 10% of its molecular weight with an average of four to five mannose and three N-acetylglucosamine residues per subunit (Bruch R. C., et al., *Biochemistry,* 1982, 21, 21, 5334).

In WO2009016031 in the name of the Applicant, was reported for the first time a chemically oxidized avidin named OXavidin$_{HABA}$, (herein named oxidized avidin), that had higher permanence in injected tissues compared to wild type avidin as a consequence of the formation of chemical linkages between the oxidized avidin aldehyde groups and the tissue protein amino groups. Said oxidized avidin could be administered directly into the diseased tissue either alone, in which case a second step for delivering the biotinylated active therapeutic agent was necessary, or as a complex with the therapeutic agent. It is important to note that in said document the oxidized avidin was administered locally by means of injection rendering impractical a homogeneous whole lung conditioning. This patent application opened a new era by disclosing new solutions useful for the localized treatment of solid tumour cancer and degenerative or genetic diseases. Tolerability of oxidized avidin was also recently reported (Petronzelli F., et al., *Basic Clin. Pharmacol. Toxicol.,* 2011, 233).

However, even this new tool did not allow to tackle those widely diffuse and/or inoperable lung diseases, notably because of the peculiarity of the lung tissue that is not easily treated by injection and because of the inadequacy of surgical procedures in reaching difficultly accessible areas of the diseased tissue. In particular, bronchioloalveolar cancer (BAC), also known as lepidic lung cancer is a form of neoplasia affecting the surface of bronchus and alveoli that might benefit from a topical therapy delivered by aerosol (Anami Y., et al., *J. Thorac. Oncol.,* 2009, 4, 8, 951).

Figure 1:
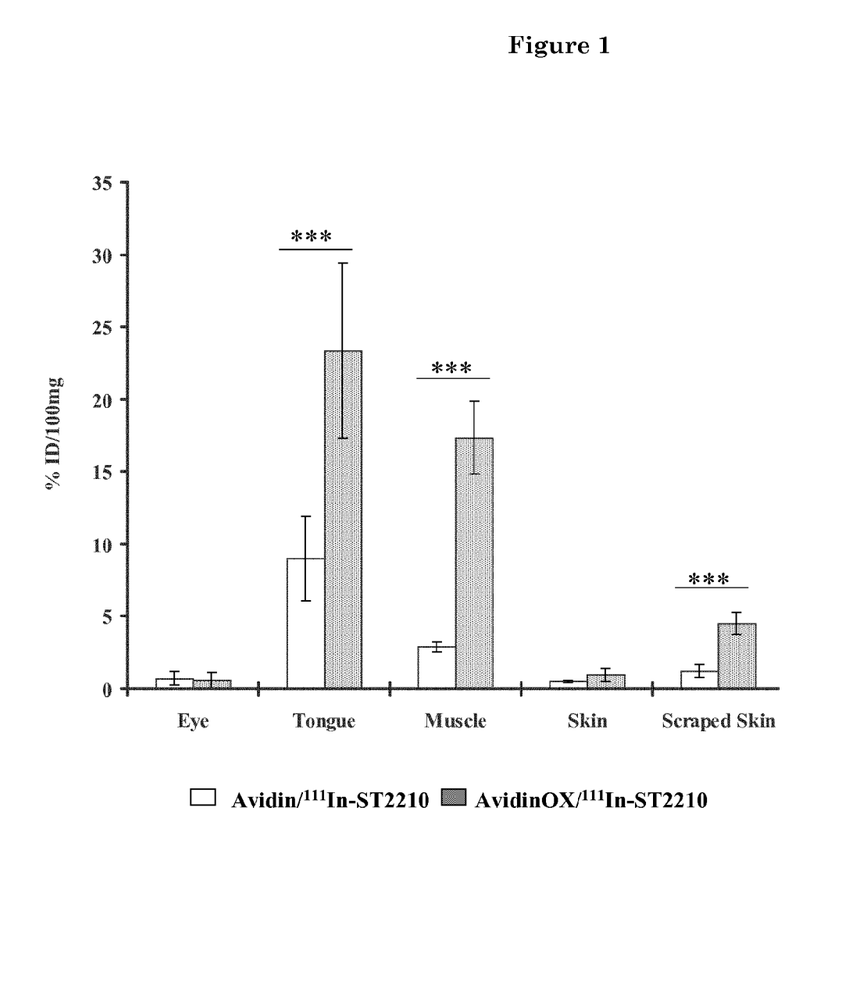
Figure 2:
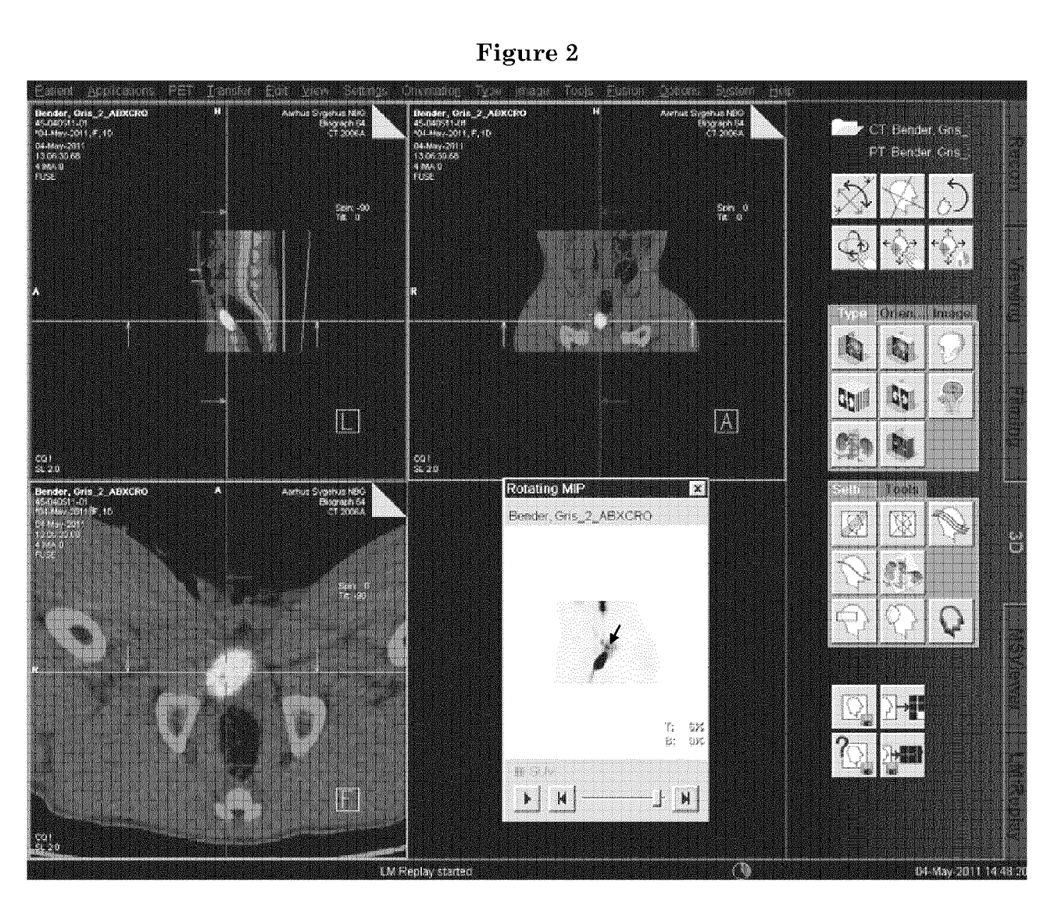
Figure 3:
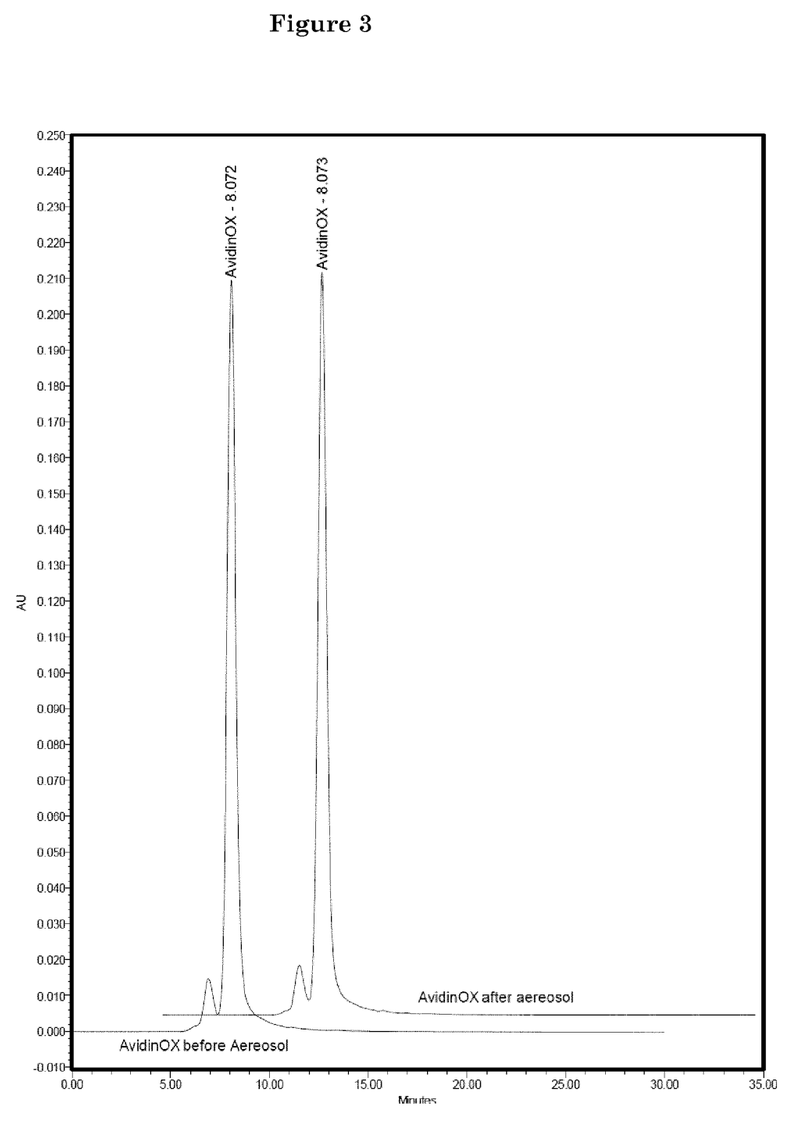

As mentioned above, it has now been found that oxidized avidin can efficiently reach and link to the lung tissue through aerosol administration. This result was not predictable based on the data of WO2009016031 and further investigation showed that the intra-tissue injection was a requirement for the oxidized avidin linkage to the tissues. In fact, deposition of oxidized avidin on intact skin or eye was not sufficient to observe a linkage (FIG. 1). Linkage of the oxidized avidin was confirmed to occur only on tissue proteins exposed by surgery also in the pig bladder (FIG. 2). Moreover, nebulised oxidized avidin was found bound to the lung but not to the trachea thus indicating a specific and unpredictable linkage event in this organ (Table 1).

The terms "AvidinOX" or "AvidinOX®" or "OXavidin$_{HABA}$," refer to the chemically oxidized avidin according to example 1 of WO2009016031. The expression "oxidized avidin" refers to a chemically oxidized avidin as claimed in WO2009016031 (i.e., an oxidized avidin in which at least one mannose residue per avidin molecule is replaced by a residue of the following formula wherein said oxidized avidin contains about 8 to 15 aldehyde moieties and has a thermal stability equal or greater than 78° C. Alternatively, the expression "oxidized avidin" also refers to a compound that was obtained by oxidation of avidin in the presence of the ligand HABA in order to prevent from oxidation tryptophan residues that are involved in the biotin-binding site.

The expression "anticancer agent" means an agent capable of fighting tumours. A non-exhaustive list of anticancer agents consists of chemotherapeutic drugs, monoclonal antibodies, radiolabelled compounds, effector cells, toxins, cytokines, viral and plasmid vectors, RNA inhibitors and anticancer cells.

The terms "aerosol", "aerosolised", "inhalable" and "nebulised" all refer to the same concept of breaking into small aerosol droplets, medical solutions/suspensions to enable them to be directly and efficiently inhaled from the mouth.

The expressions "for conditioning the lung", "lung conditioning agent" and "preconditioned lungs" refer to the concept of enabling lung cells to interact with biotinylated therapeutic agents through oxidized avidin interaction that would have been inhaled in beforehand.

In particular, the expression "for substantially wholly conditioning the lung" means that once administered, the oxidized avidin can be detected in at least 95% of the lung.

Therefore, an object of the present invention resides in a pharmaceutical inhalable composition comprising:
  a) the oxidized avidin according to claim 1 or 2,
  b) a sterile buffer solution at acidic pH, wherein said buffer is preferably sodium acetate, and optionally
  c) a non-ionic agent selected from the group comprising mannitol, glycerol, glucose, lactose, trehalose, sucrose, propylene-glycol, sorbitol, xylitol, polyethylene-glycol, ethanol and isopropanol;
wherein said pharmaceutical composition is delivered through inhalation after nebulization.

In a preferred embodiment "acidic pH" means that the pH is comprised between 5.0 and 6.9.

In a more preferred embodiment "acidic pH" means that the pH is comprised between 5.0 and 6.0.

In an even more preferred embodiment "acidic pH" means that the pH is comprised between 5.0 and 5.5.

In a further embodiment, the pharmaceutical inhalable composition is freeze-dried.

In a preferred embodiment the oxidized avidin is useful as a lung conditioning agent through inhalation.

In a more preferred embodiment said oxidized avidin is useful for substantially wholly conditions the lung through inhalation.

In another embodiment, delivery of oxidized avidin is followed by administration of a therapeutic agent, wherein said therapeutic agent is biotinylated.

In a preferred embodiment, the pharmaceutical inhalable composition of the invention is useful for the treatment of the following diseases: tuberculosis, Chronic Obstructive Pulmonary Disease (COPD), lung cancer in general and with particular interest on bronchioloalveolar (BAC) cancer, asthma, lung alveolitis, lung inflammatory diseases, cystic fibrosis and alpha-1-antitrypsin deficiency.

In a further preferred embodiment, the pharmaceutical inhalable composition of the invention is useful for the treatment of primary lung cancer in multi-focal or metastatic form.

In a still further preferred embodiment, the biotinylated therapeutic agent is a biotinylated adduct of an anticancer agent.

In a still further preferred embodiment, the biotinylated anticancer agent is a biotinylated adduct of well-known anti-cancer drugs selected from the group comprising anti-EGFR, anti-CEA, anti-MUC1, anti-EpCAM, anti-cMET, anti-CTL4 monoclonal antibodies, TNF, TRAIL, Tweak, gamma interferon, G-CSF, GM-CSF, IL-2, IL-12 or chemotherapeutics.

In an even more preferred embodiment, said anticancer agent is radioactive derivative selected from the group comprising of radiolabelled biotin-DOTA (ST2210). The latter was described in the patent application WO2002066075.

In a still more preferred embodiment, the radioisotope used to label biotin-DOTA is selected from the group comprising $^{52}$Fe, $^{52m}$Mn, $^{55}$Co, $^{64}$Cu, $^{67}$Cu, $^{67}$Ga, $^{68}$Ga, $^{99m}$Tc, $^{111}$In, $^{123}$I, $^{125}$I, $^{131}$I, $^{32}$P, $^{47}$Sc, $^{90}$Y, $^{109}$Pd, $^{111}$Ag, $^{149}$Pm, $^{186}$Re, $^{188}$Re, $^{211}$At, $^{212}$Pb, $^{212}$Bi and $^{177}$Lu.

In another more preferred embodiment, said anticancer agent is a biotinylated adduct of well-known anti-cancer drugs selected from the group consisting of viral or plasmid vectors, RNA inhibitors or anti-cancer effector cells.

In another preferred embodiment the biotinylated agent is an agent useful for the treatment of lung inflammatory diseases and is a biotinylated adduct of well-known anti-inflammatory drugs anti-inflammatory agent selected from the group comprising anti-TNF, anti-Tweak, anti-IL-17, anti-IL-23, anti-IL-6, anti-IL-1 monoclonal antibodies, IL-10 or chemokines.

In another preferred embodiment for lung genetic diseases, a therapeutic agent is a biotinylated adduct of known deficient protein like CFTCR in cystic fibrosis alpha-1-antitrypsin.

A further preferred embodiment consists in a kit comprising the pharmaceutical inhalable composition mentioned herein-above, wherein the latter is either freeze-dried or dissolved in a sterile buffer solution.

In a further more preferred embodiment said kit comprises the pharmaceutical inhalable composition mentioned herein-above and a nebulizer.

The amount of oxidized avidin which is required to achieve a therapeutic effect will, of course, vary with the subject under treatment, and the particular disorder or disease to be treated. It will further depend on the efficiency of the nebulizer used and the deposition of the aerosol droplets in the lung. Suitable concentrations of oxidized avidin within the solution for nebulisation can be in the range of 0.005% to 0.5% (w/v) (i.e. 0.05 mg/ml to 5 mg/ml).

Non-ionic agent can be used for adjusting the osmolality of the solution for nebulisation. Examples of non-ionic agents for adjusting the osmolality, which can be used in the present invention are selected from the group comprising mannitol, glycerol, glucose, lactose, trehalose, sucrose, propylene-glycol, sorbitol, xylitol, polyethylene-glycol, ethanol and isopropanol.

Besides the non-ionic agent herein above mentioned, the invention may contain one ore more additional suitable excipients. Suitable excipients, which can be mentioned include agents for modifying the pH of the solution and optionally preservatives.

The formulation of the invention may be distributed in suitable containers such as multidose vials or, preferably, unit dose vials for single dosage administration. The solution for nebulisation of the present invention can be obtained as follows: oxidized avidin of a first vial can be dissolved by addition of sterile sodium acetate solution at pH 5.5 of a second vial.

The formulations of the invention are intended for administration by nebulisation using suitable apparatus instrument that is capable of generating very fine liquid droplets for inhalation into the lungs. Suitable instruments are for example jet nebulisers or ultrasonic nebulisers.

DESCRIPTION OF THE DRAWINGS

FIG. 1:

It shows the tissue residence of the complex oxidized avidin/$^{111}$In-ST2210 in the eye (drop deposition), tongue (i.m. injection), limb (i.m. injection), skin (drop deposition), scraped skin (drop deposition).

FIG. 2:

It shows the linkage of intravenously injected 68-Ga-ST2210 to a surgical lesion performed in the bladder of a pig to simulate the removal of a human superficial bladder carcinoma (arrow). The image was obtained 4 hours after 68-Ga-ST2210 injection, by Positron Emission Tomography (PET).

FIG. 3:

It shows the chemical integrity of oxidized avidin after having been nebulised for 1 hour in a 100 mM sodium acetate solution at pH 5.5 and without excipient.

FIG. 4:

It shows, at T=2 hours and T=24 hours, the distribution of intravenously injected $^{111}$In-ST2210 in various organs of mice which have received 24 hour before oxidized avidin or vehicle through inhalation.

FIG. 5:

Immunochemistry with mouse anti-avidin antibody of lung sections, 24 hours after oxidized avidin aerosol exposure.

FIG. 6:

PET imaging of $^{64}$Cu-ST2210 intravenously injected mice which were exposed to oxidized avidin aerosol 24 hours before.

FIG. 7:

EGFR+ A431 cells incubated with biotinylated cetuximab at the dose of 5 µg, 0.05 µg, 0.05 ng and 0.05 pg/ml for 1 hour in PBS without (a) or with (b) pre-treatment with oxidized avidin.

FIG. 8:

It shows the inhibition of proliferation of A431 cell line with biotinylated cetuximab with or without prior treatment with oxidized avidin.

FIG. 9:

It show a cytofluorimetry analysis of the induction of apoptosis by biotinylated cetuximab on two cell lines, one expressing high level of EGFR (i.e., A431) and one which does not express EGFR (i.e., SKMe128) with or without treatment with oxidized avidin.

FIG. 10:

It shows the inhibition of proliferation induced by biotinylated cetuximab with or without pre-treatment with AvidinOX on A431, A549 (i.e., lung carcinoma expressing low levels of EGFR, KRAS mutated) and SKMe128 cells.

EXAMPLES

Example 1

Balb/c mice of about 20 g were treated in the indicated sites with a solution of avidin or oxidized avidin as obtained following the procedure described at example 1 of WO2009016031 (3.0 mg/ml dissolved in 100 mM sodium acetate, pH 5.5) pre-complexed with $^{111}$In-ST2210. Twenty four hours after injection/deposition, the mice were sacrificed by $CO_2$ asphyxia and the treated sites analysed by means of a gamma counter. Data are reported in FIG. 1, and are expressed as the % of injected dose/100 mg of tissue (% ID/100 mg). Results show a statistically significant higher amount of oxidized avidin/$^{111}$In-ST2210 complex in injected tongue, limb muscle and on the topically treated scraped skin compared to the Avidin/$^{111}$In-ST2210 complex. However, deposition of the oxidized avidin/$^{111}$In-ST2210 or Avidin/$^{111}$In-ST2210 complex on normal skin or in the eye did not lead to similar results, indicating that the complex does not bind to external tissue surfaces and consequently that a surgical operation is required to take advantage of the binding properties of oxidized avidin either as single agent when complexed with a biotinylated agent.

Example 2

Anesthetised female pig of about 40 kg was subjected to surgery to generate two 2 cm superficial lesions on the bladder wall. Then, 30 ml of oxidized avidin solution (3.0 mg/ml dissolved in 100 mM sodium acetate, pH 5.5) were instilled via a catheter and let interact for 1 hour. Bladder was then washed with saline and 0.5 µg 68-Ga-ST2210 was i.v. administered. After 4 hours the pig was subjected to PET. Results as shown in FIG. 2, demonstrate that only the region that had been subjected to surgery (i.e., 2 mm lesion) enabled the binding of oxidized avidin, meanwhile intact bladder tissue proved to be completely inert to the aldehyde moieties of oxidized avidin. Those surprising data are however, in agreement with those of example 1 wherein non-surgically damaged tissue were inert to oxidized avidin.

Example 3

A 100 mM sodium acetate solution at pH 5.5 containing oxidized avidin at the concentration of 3.0 mg/ml was nebulised by means of a the Nose-Only inExpose System (Scireq-EMKA technologies) for 1 hour at room temperature. The particle size of the protein solution midst was 5 μm. The nebulised solution was recovered in a falcon tube and analyzed by HPLC. Data in FIG. 3 show the same elution profile for the oxidized avidin solution pre and post nebulisation indicating perfect stability of the protein. This result was not obvious as many proteins and nucleic acid need extensive formulation studies to select a condition that preserves integrity and potency of such drugs during nebulisation (Geller D. E., et al., *J. Aerosol Med. Pulm. Drug Deliv.,* 2010, 23 Suppl 1, S55; Markovic S. N., et al., *Am. J. Clin. Oncol.,* 2008, 31, 6, 573; Choi W. S., et al., *Proc. Natl. Acad. Sci.,* 98, 20, 11103).

It was very interesting to note that notwithstanding the fact that aldehyde derivatives are highly susceptible to hydration in the presence of water, no such phenomena was observed during oxidized avidin nebulisation process. Indeed, the number of aldehyde moieties per molecule, as determined by Purpald's method (Quesenberry M. S., et al., Anal. Biochem., 1996, 234, 1, 50), was found to be substantially the same (considering the variability of the assay) before and after nebulisation at both pH 5.0 and pH 5.5, with and without mannitol excipient as demonstrated by data in Table 1.

TABLE 1

| Oxidized avidin batch | Number of CHO moieties per molecule: Before nebulisation | After nebulisation |
|---|---|---|
| Mannitol formulation pH 5.0 | 19.7 | 19.2 |
| Mannitol formulation pH 5.5 | 17.1 | 19.4 |
| Acetate buffer formulation pH 5.5 | 16.4 | 16.7 |

Example 4

Biological activity and biostribution of nebulised oxidized avidin were evaluated in rat by measuring the uptake of 5 μg of $^{111}$Indium radiolabelled biotinDOTA (i.e., $^{111}$In-ST2210) intravenously injected, 24 hours after oxidized avidin, avidin (3.0 mg/ml solution, 0.8 ml/min, 1 hour nebulisation) or vehicle inhalation exposure, in the lung and non target organs.

Twenty Sprague Dawley rats were divided in three different groups. Each group received the following treatments:

- the first group (made of 4 rats) was exposed to nebulised vehicle only (i.e., 100 mM sodium acetate solution at pH 5.5) and 24 hours later the rats received a 5 μg i.v. dose of $^{111}$In-ST2210 in 0.5 ml of saline.
- the second group (made of 8 rats) was exposed to nebulised avidin (about 10 mg/kg) in a 100 mM sodium acetate solution at pH 5.5 and 24 hours later the rats received a 5 μg i.v.dose of $^{111}$In-ST2210 in 0.5 ml of saline.
- the third group (made of 8 rats) was exposed to nebulised oxidized avidin (about 10 mg/kg) in a 100 mM sodium acetate solution at pH 5.5 and 24 hours later the rats received a 5 μg i.v. dose of $^{111}$In-ST2210 in 0.5 ml of saline.

All rats were sacrificed 2 hours after the i.v. administration of $^{111}$In-ST2210, and samples of blood, spleen, kidney, liver, stomach, brain, trachea, and tissue samples of different portions of lung were collected, weighed and analyzed with the use of a gamma-counter (Perkin Elmer). Data were expressed as the % of injected dose/gram of tissue (% ID/g).

As shown in Table 2, oxidized avidin inhalation enables to increase in a statistically significant fashion $^{111}$In-ST2210 concentration in the lung, meanwhile other organs did not show any statistical differences of concentration of $^{111}$In-ST2210 compared to avidin or vehicle groups.

TABLE 2

| | $^{111}$In-ST2210 % ID/g | | |
| --- | --- | --- | --- |
| Groups | Vehicle | Avidin | Oxidized avidin |
| Blood | 0.011 ± 0.005 | 0.009 ± 0.005 | 0.012 ± 0.004 |
| Spleen | 0.105 ± 0.159 | 0.027 ± 0.003 | 0.032 ± 0.002 |
| Kidney | 0.426 ± 0.082 | 0.378 ± 0.048 | 0.414 ± 0.033 |
| Liver | 0.046 ± 0.009 | 0.041 ± 0.007 | 0.051 ± 0.005 |
| Stomach | 0.031 ± 0.011 | 0.067 ± 0.085 | 0.276 ± 0.246 |
| Brain | 0.002 ± 0.001 | 0.002 ± 0.000 | 0.002 ± 0.000 |
| Trachea | 0.021 ± 0.007 | 0.022 ± 0.008 | 0.029 ± 0.007 |
| Lung | 0.024 ± 0.004 | 0.023 ± 0.006 | 0.054 ± 0.009*** |
| Lung sn | 0.024 ± 0.004 | 0.023 ± 0.006 | 0.053 ± 0.008*** |
| Lung dx (caudal lobe) | 0.024 ± 0.004 | 0.022 ± 0.006 | 0.055 ± 0.009*** |
| Lung dx (cranial, middle and accessory lobe) | 0.025 ± 0.004 | 0.023 ± 0.005 | 0.055 ± 0.011*** |

***$p < 0.001$ one way Anova versus avidin

Example 5

A biodistribution experiment aimed at determining the lung uptake selectivity and stability of $^{111}$In-ST2210 was conducted. Balb/c mice of about 20 g (5 mice/group) were exposed to nebulised (i.e., by means of Nose-Only inExpose System—Scireq—EMKA technologies) oxidized avidin (3 mg/ml solution) or vehicle (3 ml) for 1 hour; 1 hour exposition corresponding to about a 90 mg/kg dose. Twenty four hours after, all mice received $^{111}$In-ST2210 intravenously (i.e., 1 μg in 0.2 ml of saline), and after further 2 or 24 hours, the animals were sacrificed by $CO_2$ asphyxia. The lung and non target organs were collected weighed and counted in a gamma counter. Data were expressed as the % of injected dose/gram of tissue.

Figure 4:
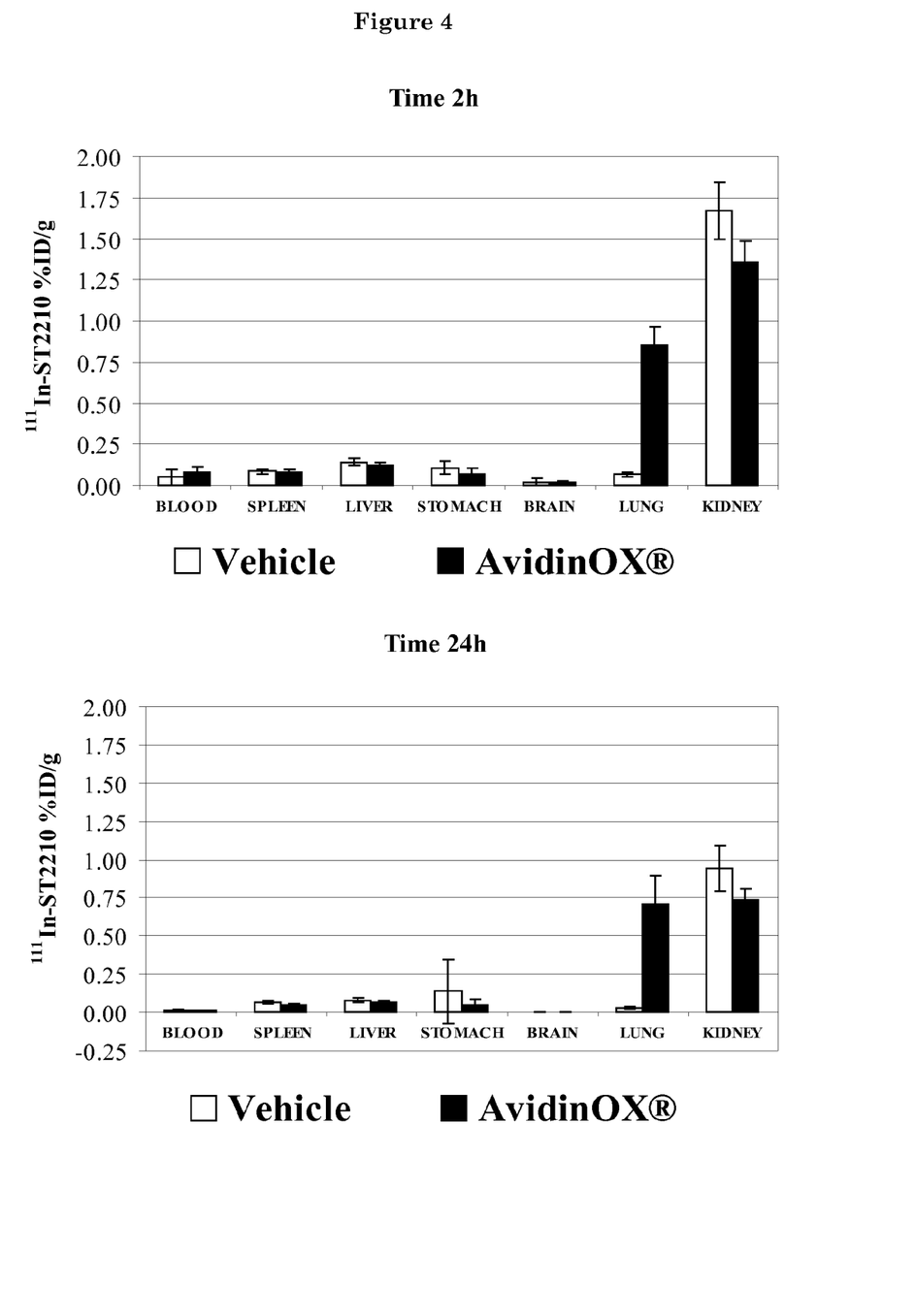

Results, as exposed in FIG. 4, demonstrate a specific and significant uptake of $^{111}$In-ST2210 only in the lung which had been pre-treated with oxidized avidin.

Example 6

Balb/c mice of about 20 g were exposed to nebulised oxidized avidin according to the protocol described at example 3, and were sacrificed by asphyxia 24 hours after. The lungs were removed and fixed in formalin and paraffin embedded. Serial sections obtained by means of a microtome were processed and incubated with a HRP-conjugated rabbit anti-avidin antibody (GeneTex, USA) and then with DAB substrate.

Figure 5:
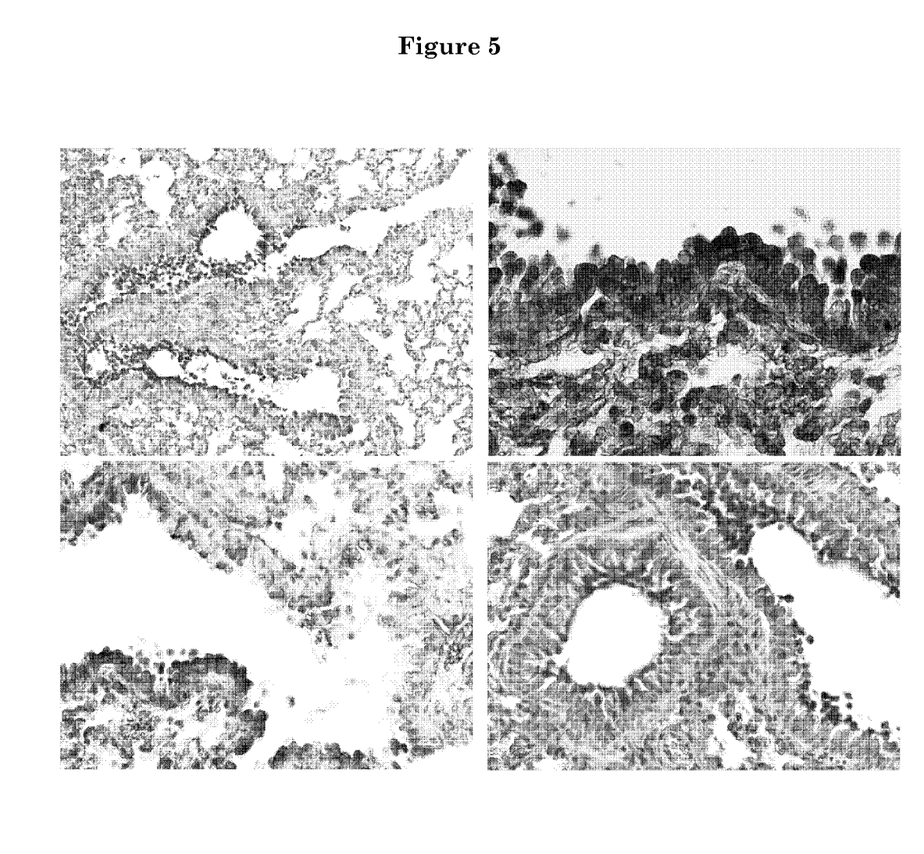

FIG. 5 shows the presence of oxidized avidin at broncho/epithelial level down to terminal bronchioles. This distribution was found to be homogenous in all lung compartments.

Example 7

Figure 6:
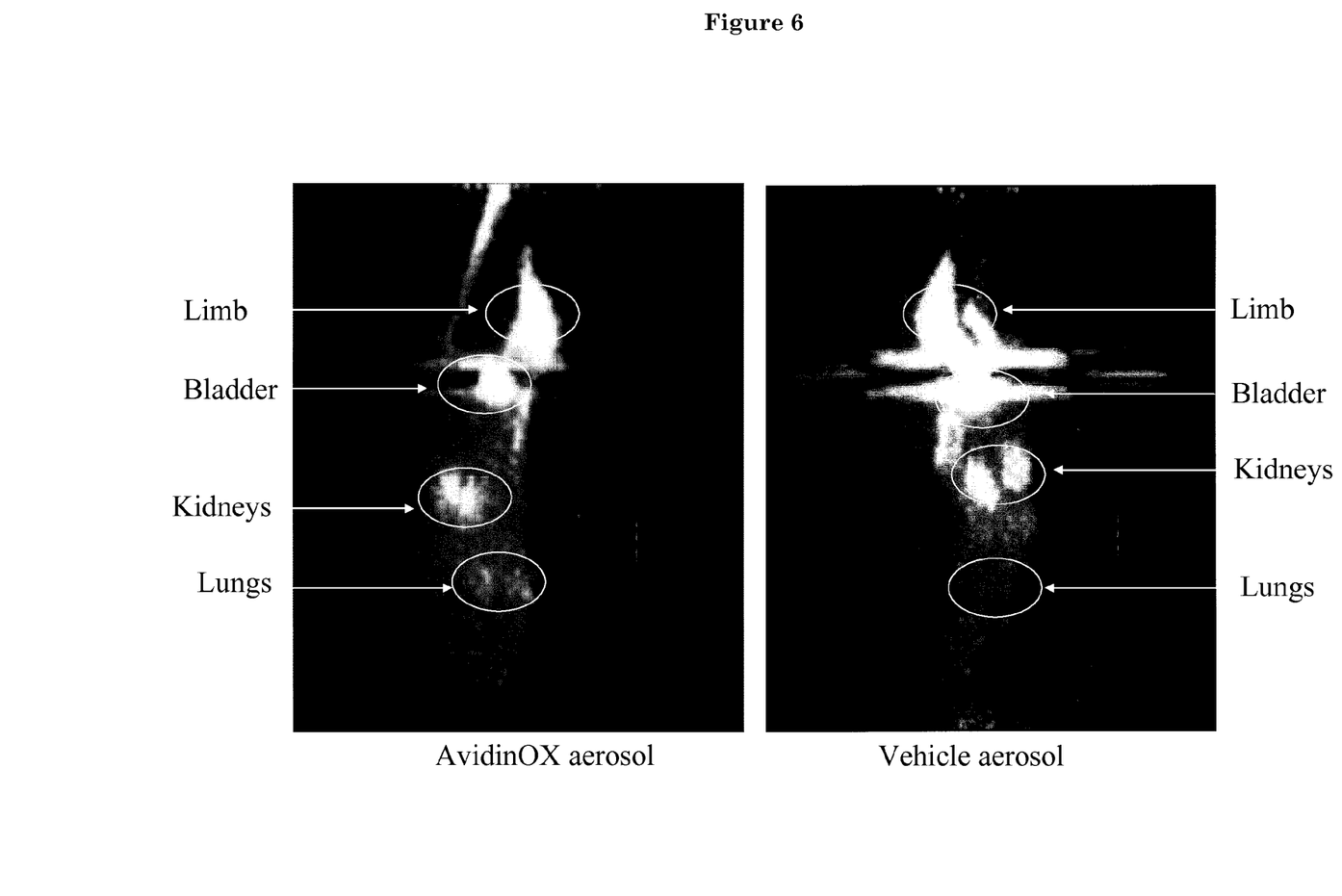

Balb/c mice of about 20 g were exposed to nebulised oxidized avidin or vehicle according to the protocol described at example 5. After 24 hours, they received an intravenous 1 μg dose of $^{64}$Cu-ST2210. $^{64}$Cu-ST2210 distribution was examined by PET imaging 4 hours after. FIG. 6 shows the presence of a radioactive signal in the lungs of the mouse pre-treated with nebulised oxidized avidin but not in the lungs of a vehicle treated mouse. Kidneys, bladder are visible in both groups of mice. This observation is consistent with the physiological elimination of ST2210 at that time point. A radioactive signal in one limb is also visible in both groups of mice since they had been i.m. pre-treated with oxidized avidin at the time of aerosol in order to have an internal positive control in the experiment.

Example 8

Human EGFR$^+$, epidermoid carcinoma cells A431 were incubated in PBS for 1 hour with 1 ml of an anti-EGFR monoclonal biotinylated antibody (i.e., biotinylated cetuximab) in the dose range of 0.05 pg/ml to 5 μg/ml. In one experiment the cells were previously incubated with oxidized avidin meanwhile in the first experiment, cells were only treated with biotinylated cetuximab.

Figure 7:
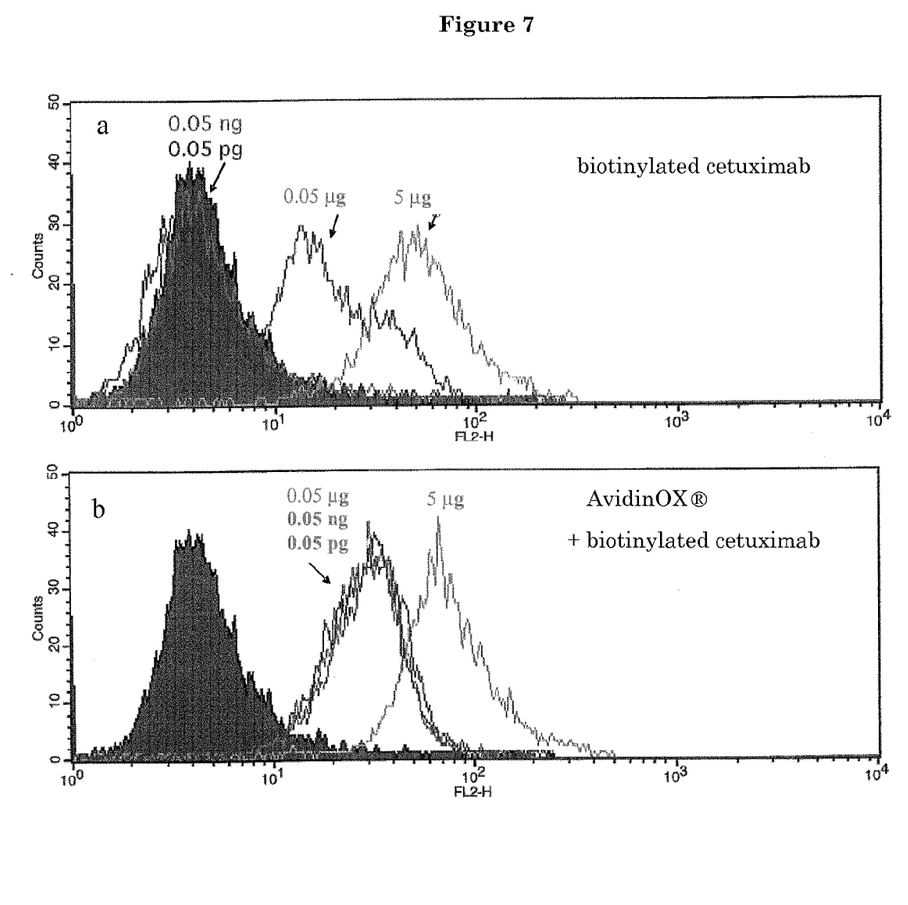

After washings, biotinylated cetuximab binding was detected by cytofluorimetry after incubation with a mouse anti-human antibody conjugated with phycoerythrin (PE). As demonstrated in FIG. 7, in the presence of oxidized avidin, the binding to A431 cells of low doses of biotinylated cetuximab such as 0.05 ng and 0.05 pg/ml is still visible.

Example 9

Figure 8:
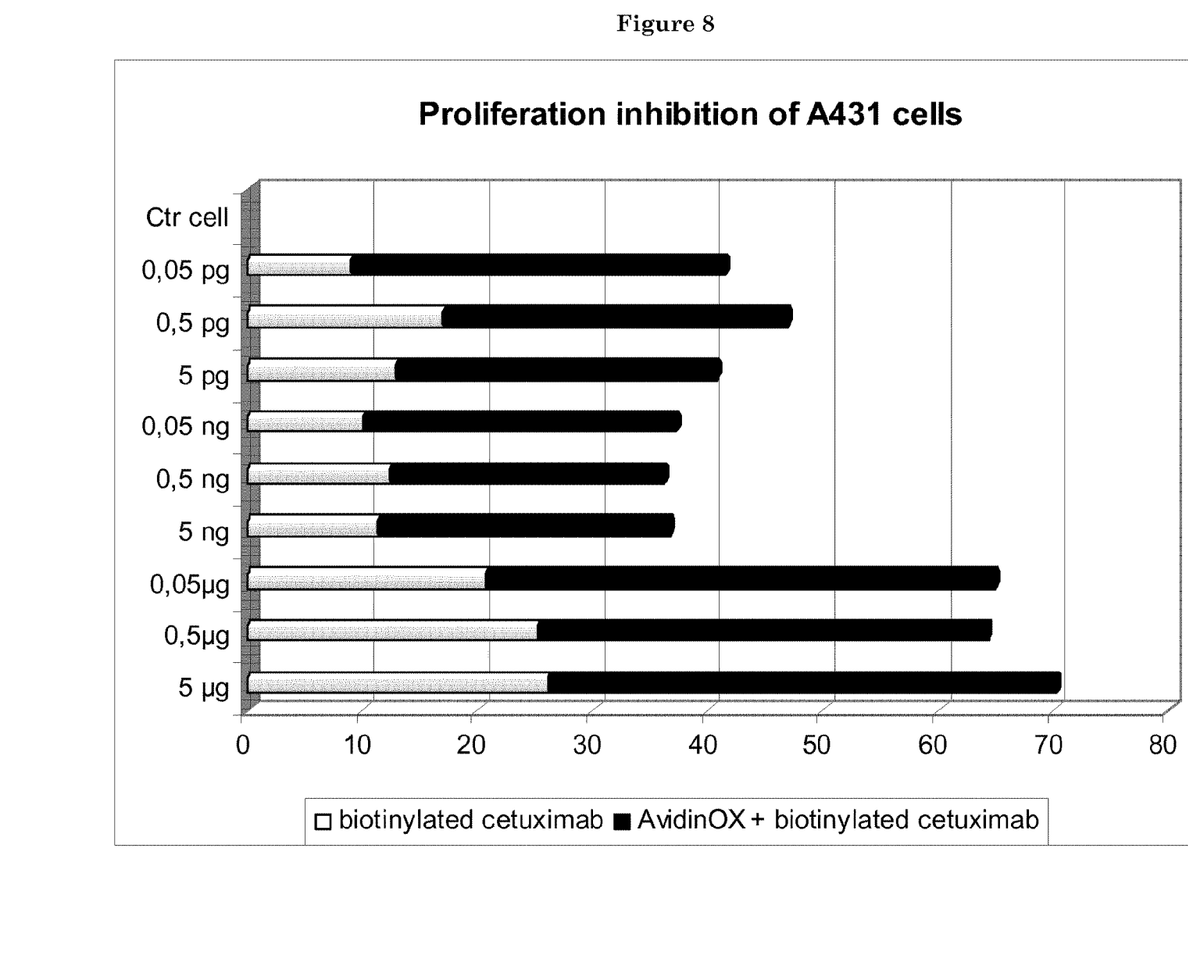

Data reported in FIG. 8 show that the anti proliferative activity of biotinylated cetuximab (experiment being conducted as reported in example 8) was increased at least 3 times owing to its immobilization through binding to the membrane bound oxidized avidin even at doses as low as 0.05 ng and 0.05 pg/ml. Proliferation inhibition was measured by Cell Titer Glow assay, Promega. Data are expressed as % of inhibition of cell proliferation in the absence of oxidized avidin (i.e., white bars) or in its presence (i.e., black bars). Moreover, as also previously reported (Petronzelli F., et al., Basic Clin. Pharmacol. Toxicol., 2011, 233), oxidized avidin did not affect cell proliferation as observed in a comparison experiment involving medium only (data not shown).

Example 10

Figure 9:
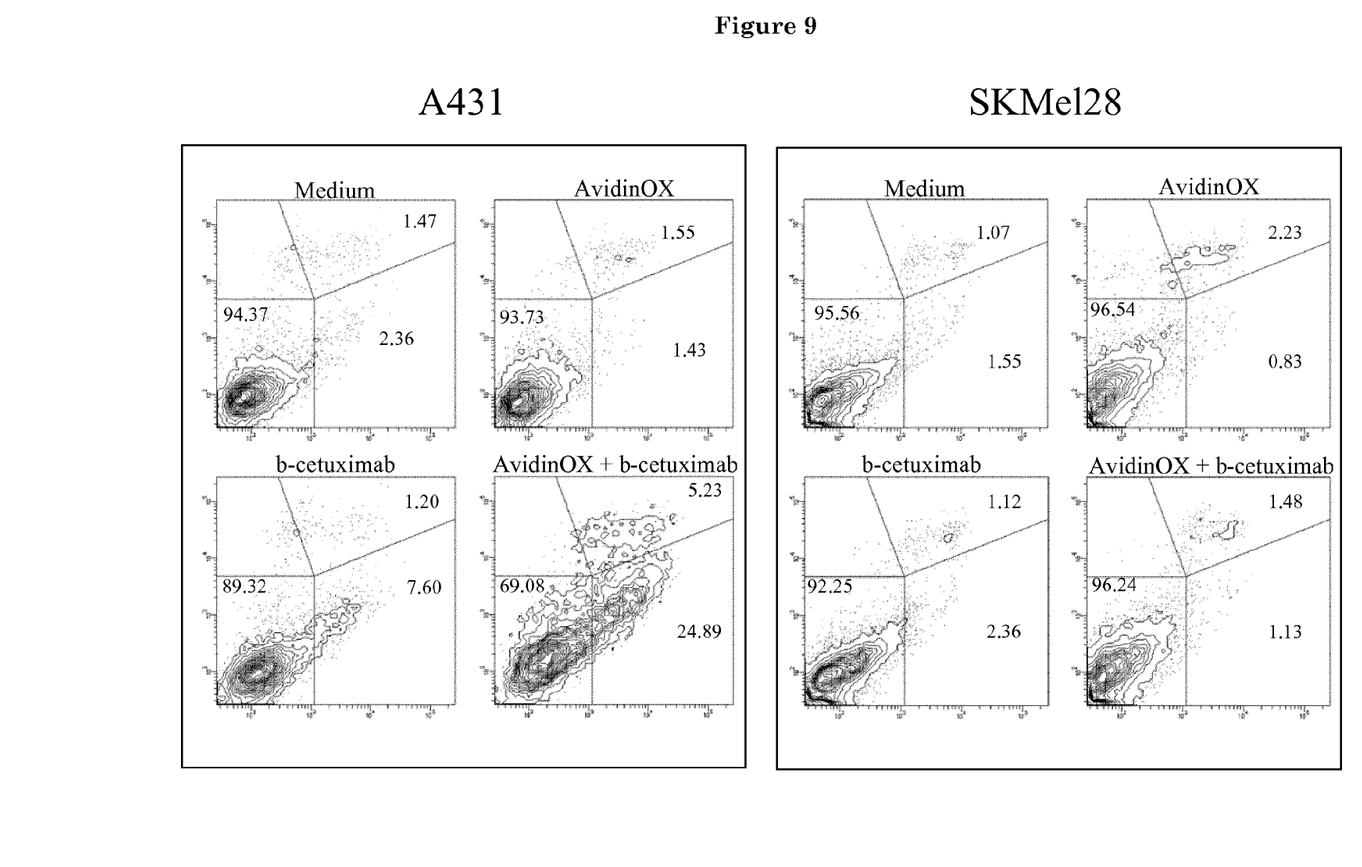

Induction of apoptosis by biotinylated cetuximab with or without pre-treatment with AvidinOX was tested on EGFR$^+$ A431 cells (vulvar squamous cell carcinoma, expressing high levels of EGFR, KRAS wild-type) and EGFR$^-$ SKMel28 cells (which do not express EGFR). The cells were incubated for 15 minutes with biotinylated cetuximab (b-cetuximab) in the presence or absence of AvidinOX pre-treatment. After washings, the cells were incubated in complete medium for 18 hours. Annexin V positive cells were analysed by cytofluorimetry with FITC-Annexin V apoptosis detection kit I (BD Pharmingen). Data in FIG. 9 indicate that the pro-apoptotic effect of biotinylated cetuximab is increased at least 3 times when AvidinOX is anchored on the membrane of the EGFR$^+$ cells but not of the EGFR$^-$ cells thus indicating the specificity of pro-apoptotic activity of the AvidinOX-anchored biotinylated cetuximab.

Example 11

Figure 10:
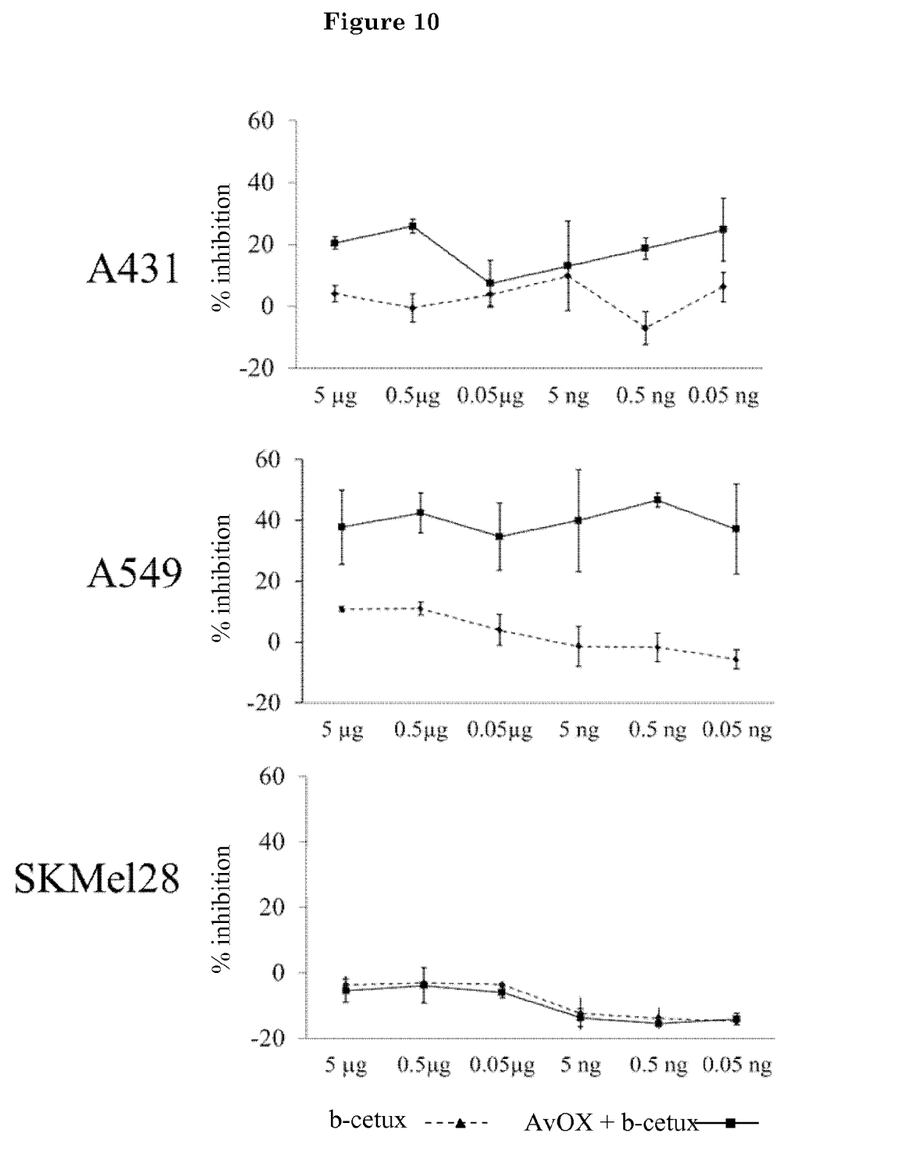

Inhibition of proliferation by biotinylated cetuximab with or without pre-treatment with AvidinOX was tested on A431, A549 (i.e., lung carcinoma, low EGFR, KRAS mutated) and SKMel28 cells. For testing the effect of anchored biotinylated cetuximab on cell proliferation, 5×10$^5$ A431, A549 and SKMel28 cells, with and without pre-incubation with AvidinOX, were seeded in 96 wells micro-titer plates (2×10$^3$ cells/well) in DMEM, 10% FCS. After adhesion, 100 µl of biotinylated cetuximab were added, in triplicates, in the range of 0.05 pg/ml to 5 µg/ml, in DMEM 1% FCS. The cells were washed after 15 minutes and cultivated for 48 hours in DMEM 1% FCS. Cell viability was detected by CellTiter-Glow® (Promega). Data in FIG. 10 show that biotinylated cetuximab was able to inhibit proliferation of cells expressing high levels of EGFR (i.e., human vulvar carcinoma A431 cells) and low levels of EGFR (i.e., KRAS mutated, human lung adenocarcinoma A549 cells) but not proliferation of EGFR$^-$ cells (SKMel28). Surprisingly, such effects were significantly improved when biotinylated cetuximab was AvidinOX-anchored on the cell surface of these EGFR$^+$ cells.

The invention claimed is:

1. A method for treating a lung cancer disease comprising:
   administering to a patient in need thereof an effective amount of oxidized avidin via nebulization and inhalation of a pharmaceutical inhalable formulation comprising oxidized avidin, a sterile buffer solution comprising sodium acetate at pH of from 5.0 to 6.9, and a non-ionic agent selected from the group consisting of mannitol, glycerol, glucose, lactose, trehalose, sucrose, propylene-glycol, sorbitol, xylitol, polyethylene-glycol, ethanol and isopropanol, wherein the oxidized avidin is at a concentration of from 0.005% to about 0.5% (w/v), and thereafter
   administering to the patient a biotinylated therapeutic agent selected from the group consisting of radioactive agents, monoclonal antibodies, cytokines, chemokines, enzymes, chemotherapeutics, viral or plasmid vectors and cells.

2. The method according to claim 1, wherein the biotinylated therapeutic agent is a biotinylated derivative of a monoclonal antibody selected from the group consisting of anti-EGFR, anti-CEA, anti-MUC1, anti-EpCAM, anti-cMET, anti-CTL4, anti-TNF, anti-Tweak, anti-IL-17, anti-IL-23, anti-IL-6, and anti-IL-1.

3. The method according to claim 1, wherein the biotinylated therapeutic agent is a biotinylated adduct of a cytokine selected from the group consisting of TNF, Tweak, TRAIL, gamma interferon, G-CSF, GM-CSF, IL-2, and IL-12.

4. The method according to claim 1, wherein the biotinylated therapeutic agent is a biotinylated adduct of a chemokine selected from the group consisting of CXC and CC chemokine families.

5. The method according to claim 1, wherein the biotinylated therapeutic agent is biotin-DOTA labelled with a radioisotope selected from the group consisting of $^{52}$Fe, $^{52m}$Mn, $^{55}$Co, $^{64}$Cu, $^{67}$Cu, $^{67}$Ga, $^{68}$Ga, $^{99m}$Tc, $^{111}$In, $^{123}$I, $^{125}$I, $^{131}$I, $^{32}$P, $^{47}$Sc, $^{90}$Y, $^{109}$Pd, $^{111}$Ag, $^{149}$Pm, $^{186}$Re, $^{188}$Re, $^{211}$At, $^{212}$Pb, $^{212}$Bi and $^{177}$Lu.

6. A kit comprising a pharmaceutical inhalable formulation contained in a nebulizer and comprising oxidized avidin, a sterile buffer solution comprising sodium acetate at pH of from 5.0 to 6.9, and a non-ionic agent selected from the group consisting of mannitol, glycerol, glucose, lactose, trehalose, sucrose, propylene-glycol, sorbitol, xylitol, polyethylene-glycol, ethanol, and isopropanol, wherein the oxidized avidin is at a concentration of from 0.005% to about 0.5% (w/v).

* * * * *